(12) United States Patent
Sansom et al.

(10) Patent No.: US 9,999,741 B2
(45) Date of Patent: Jun. 19, 2018

(54) RESPIRATORY GAS FLOW SENSOR WITH SAMPLING PORT

(71) Applicant: EUROPLAZ TECHNOLOGIES LIMITED, Southminster, Essex (GB)

(72) Inventors: Steve Sansom, Southminster (GB); Frede Jensen, Southminster (GB)

(73) Assignee: EUROPLAZ TECHNOLOGIES LIMITED (GB)

( * ) Notice: Subject to any disclaimer, the term of this patent is extended or adjusted under 35 U.S.C. 154(b) by 887 days.

(21) Appl. No.: 14/363,069

(22) PCT Filed: Nov. 29, 2012

(86) PCT No.: PCT/GB2012/052940
§ 371 (c)(1),
(2) Date: Jun. 5, 2014

(87) PCT Pub. No.: WO2013/083958
PCT Pub. Date: Jun. 13, 2013

(65) Prior Publication Data
US 2014/0358022 A1    Dec. 4, 2014

(30) Foreign Application Priority Data
Dec. 8, 2011 (GB) .................................. 1121143.0

(51) Int. Cl.
*A61B 5/08* (2006.01)
*A61M 16/08* (2006.01)
(Continued)

(52) U.S. Cl.
CPC ......... *A61M 16/085* (2014.02); *A61B 5/0878* (2013.01); *A61B 5/097* (2013.01);
(Continued)

(58) Field of Classification Search
CPC .... A61M 16/085; A61M 16/12; A61M 16/14; A61M 16/0003; A61M 16/0841;
(Continued)

(56) References Cited

U.S. PATENT DOCUMENTS

2001/0039833 A1* 11/2001 Engel .................... A61B 5/0878
                                                73/204.27
2003/0075178 A1*  4/2003 Claure .................. A61M 16/08
                                                128/204.18
(Continued)

*Primary Examiner* — Navin Natnithitadha
*Assistant Examiner* — Andrey Shostak
(74) *Attorney, Agent, or Firm* — Renner Kenner Greive Bobak Taylor & Weber (57) ABSTRACT

The accurate measurement of inspired and expired gas volume flow and gas composition are important in respiratory therapy. The invention provides a gas flow sensor for a ventilator comprising: a flow path extending between a first end that connects to a supply of gas and a second end that couples to a patient airway interface; and a constant temperature anemometer sensor arranged within the flow path between those ends. It further comprises a sampling port that may be coupled to a gas analyser device; and an orifice which is in fluid communication with the flow path and the sampling port so that, in use, gas may be drawn from the flow path for analysis, the gas being drawn from the flow path at a position located between the anemometer sensor and the first end.

7 Claims, 6 Drawing Sheets (51) Int. Cl.
    *A61B 5/087*     (2006.01)
    *A61B 5/097*     (2006.01)
    *A61M 16/12*     (2006.01)
    *A61M 16/14*     (2006.01)
    *A61M 16/00*     (2006.01)

(52) U.S. Cl.
    CPC .... *A61M 16/0003* (2014.02); *A61M 16/0816* (2013.01); *A61M 16/0833* (2014.02); *A61M 16/0841* (2014.02); *A61M 16/12* (2013.01); *A61M 16/14* (2013.01); *A61M 2016/0033* (2013.01); *A61M 2016/0036* (2013.01); *A61M 2206/11* (2013.01)

(58) Field of Classification Search
    CPC .......... A61M 16/0833; A61M 16/0816; A61M 2016/0033; A61M 2016/0036; A61M 2206/11; A61B 5/091; A61B 5/097; A61B 5/0878
    See application file for complete search history.

(56) References Cited

U.S. PATENT DOCUMENTS

| | | | |
|---|---|---|---|
| 2004/0069307 A1* | 4/2004 | Rich ................. | A61M 16/0463 128/207.14 |
| 2005/0137491 A1* | 6/2005 | Paz ....................... | A61B 5/097 600/543 |
| 2008/0283062 A1* | 11/2008 | Esposito, Jr. .......... | A61B 5/061 128/204.23 |
| 2010/0036272 A1* | 2/2010 | Mace .................... | A61B 5/083 600/531 |

* cited by examiner

RESPIRATORY GAS FLOW SENSOR WITH SAMPLING PORT

FIELD OF THE INVENTION

The present invention relates to a component for use in medical artificial ventilation. The combined component includes a flow sensor for the measurement of the volume of gas flow and a port for extraction of sampling gas for routing to a concentration measurement device.

BACKGROUND OF THE INVENTION

For present purpose "patient circuit" means an open or re-circulating conduit for transporting respiratory gas between a ventilator and a human or animal patient. "Tidal volume" is the volume of air inhaled and exhaled at each breath. "Deadspace" is a volumetric space in the flow sensor and associated tube connectors from which gas does not reach the patient's alveoli during inhalation and/or which buffers carbon dioxide rich gas from reaching the exhaust channel during exhalation.

Systems for measuring the gas volume flow and gas composition in respiratory therapy are well known. An example of a constant temperature anemometry flow sensor is described in U.S. Pat. No. 4,363,236, and an example of a gas sampling and analysis system is described in U.S. Pat. No. 7,341,563. Due to the fact that partial pressure of carbon dioxide in the fresh ventilation gas is practically zero, the partial pressure of carbon dioxide in the patient alveoli closely represents that in the patient blood system. Units of exhaled gas originating from the alveoli are generally the last to be washed-out, in the end-tidal volume. Other tidal gas inhaled into and out from the upper airway and lung branches does not reach the alveoli and does therefore not contain carbon dioxide that is exchanged in the current breath. Gas flow turbulence prior to reaching the side-stream sampling port causes the end-tidal gas volume to mix with other tidal gas. The effect is an under reading of the actual carbon dioxide value from the alveoli. This under reading effect can be considerable for premature and infant patients, where the end-tidal gas volume is very small. In addition to causing under-measurement of the indicator for blood carbon dioxide, the deadspace may also result in an actual increase in blood carbon dioxide, by detracting from the amount of fresh gas exchange and causing rebreathing of previously exhaled gas. One way to minimize deadspace is to 'throttle down' or reduce the cross-sectional area of the tubular bore through the flow sensor. However, this has effect of simultaneously increasing the gas flow resistance and inhibiting the effective emptying of the lung. The tube bore cross-section therefore has an optimum dimension which relates to the ventilation flow rate and volume, which in turn relates to the size of patient. Taking the smallest patients into account, the deadspace should ideally be less than 1 ml. An example of a gas sampling adapter arrangement for reducing deadspace and adverse gas mixing is described in U.S. Pat. No. 6,926,005 and in U.S. Pat. No. 7,059,322.

A further problem can exist caused by the diversion of gas flow for sampling as this can reduce accuracy in the volume flow measurement. The tidal volume in infants is 4-8 ml/kg weight. The smallest viable patients weigh down to about 300 g and may tolerate as little as 2 ml tidal volume, which at 50 breathes-per-minute equates to a volume of approximately 100 ml/min. In a severe case as described below in respect of the prior art shown in FIGS. 1 and 3 the diversion of sampling gas, on the patient side of the flow measurement site, can result in a 50% under-measurement of the actual tidal volume. Modern ventilators would register such loss as a leak at the patient interface. Ventilation is an output driven therapy, where the target tidal volume is, typically, adjusted according to patient response. On-going ventilator adjustments generally take into account and compensate for a certain amount of leak. However, the leak effect is a further level of complexity for the clinician to consider, and thereby introduces a risk of sub-optimal ventilator settings. Accidental over-distension (by too large a volume) may cause irreparable lung tissue damage. Often the patient's metabolic rate is calculated from gas volume and carbon dioxide and oxygen concentration variables. Such calculations are potentially unreliable when using leak compensated volume estimation. It is therefore desirable to eliminate tidal volume measurement errors and rogue leak measurements.

BRIEF SUMMARY OF THE INVENTION

The present invention is an improved bi-directional constant temperature anemometry flow sensor, incorporating a gas sampling port arrangement which aims to assure volume flow measurement accuracy and eliminate rogue leak measurement. The device combines the two measuring functions into a single component for reduced deadspace and weight. The new arrangement of the gas sampling port is optimised to minimise turbulence and space prior to the sampling gas diversion point.

According to a first aspect of the present invention there is provided a gas flow sensor for a ventilator comprising:

a. a flow path extending between a first end that connects to a supply of gas and a second end that couples to a patient airway interface;

b. a constant temperature anemometer sensor arranged within the flow path between those ends;

c. a sampling port that may be coupled with a gas analyser device; and d. an orifice which is in fluid communication with the flow path and the sampling port so that in use gas may be drawn from the flow path for analysis, the gas being drawn through the orifice from the flow path at a position located between the anemometer sensor and the first end.

The distance between the orifice (or an opening in the position at which the gas is drawn from the flow path if that is remote from the orifice) and the anemometer sensor is important and is preferably within the range of 3-10 mm. This distance is usually measured (parallel to the flow path) from the edge of the orifice/opening nearest the sensor to the nearest part if the sensor. If the senor comprises one or more wire arranged perpendicularly across the flow path the distance may be measured from the wire nearest the orifice. The orifice or opening leading to the orifice may be shaped to minimise turbulence in the flow past it.

The flow path may ideally be defined by a substantially straight passageway. This can help to minimises turbulence and improve flow characteristics. The passageway may be tubular and usually is of a generally circular cross section, although it may have a different cross sectional shape.

In the gas flow sensor the anemometer sensor may comprise one or more wire arranged perpendicularly across, and substantially centrally within, the flow path. This sensor type often may have two or more such parallel wires. The operation of such sensors is well known.

The cross-sectional area of the flow path may be minimized to the smallest effective size according to the patient volume flow rate. This also reduces the deadspace volume.

Preferably a mesh is located across the flow path adjacent the first end and/or second end. One or more mesh may be provided across both ends and a mesh may comprise one or more overlaid layers mesh material. The mesh, or like component, helps to promote laminar flow and to protect the delicate sensor wires.

Whilst the present invention may be used for any type of gas it is ideally suited to use where the gas is air, or a mixture of air and at least one other gas or vaporised material.

According to a second aspect of the present invention there is also provided a method of drawing sampling gas from the flow path of a ventilator including a constant temperature anemometer sensor arranged within that flow path, the method comprising:
- providing an orifice which is in fluid communication with the flow path on the upstream side of the anemometer sensor wires; and,
- drawing gas through the orifice from the flow path and passing to a gas analyser device for analysis.

Ideally the orifice if provided at a distance of 3-10 mm from the sensor wires.

BRIEF DESCRIPTION OF THE SEVERAL VIEWS OF THE DRAWINGS

The present invention will now be described by way of example with reference to the accompanying drawings in which FIGS. 1-3 represent prior art and FIGS. 4-6 show one embodiment of the present invention. In the drawings:

DETAILED DESCRIPTION OF THE INVENTION

Figure 1A:
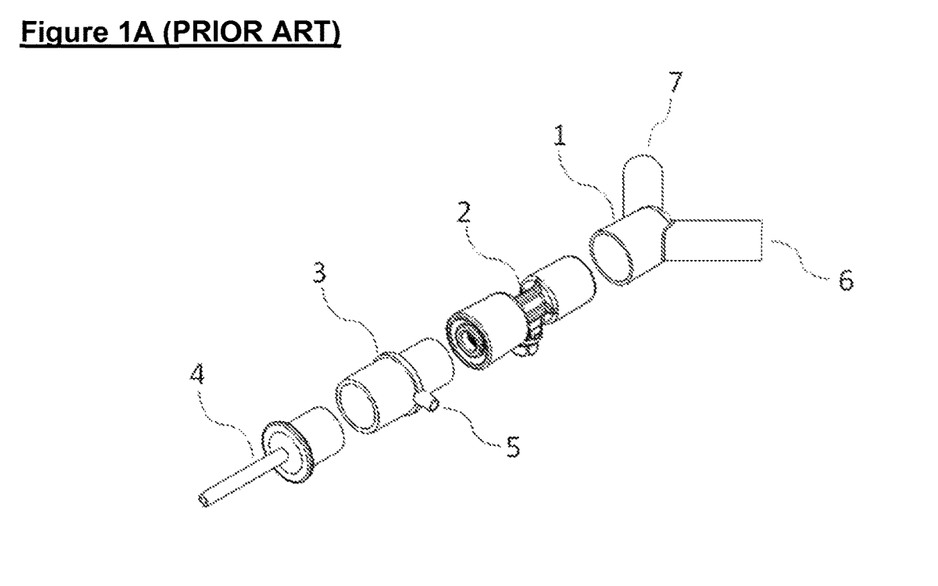
FIG. 1A shows an exploded perspective view of a first prior art port configuration.
Figure 1B:
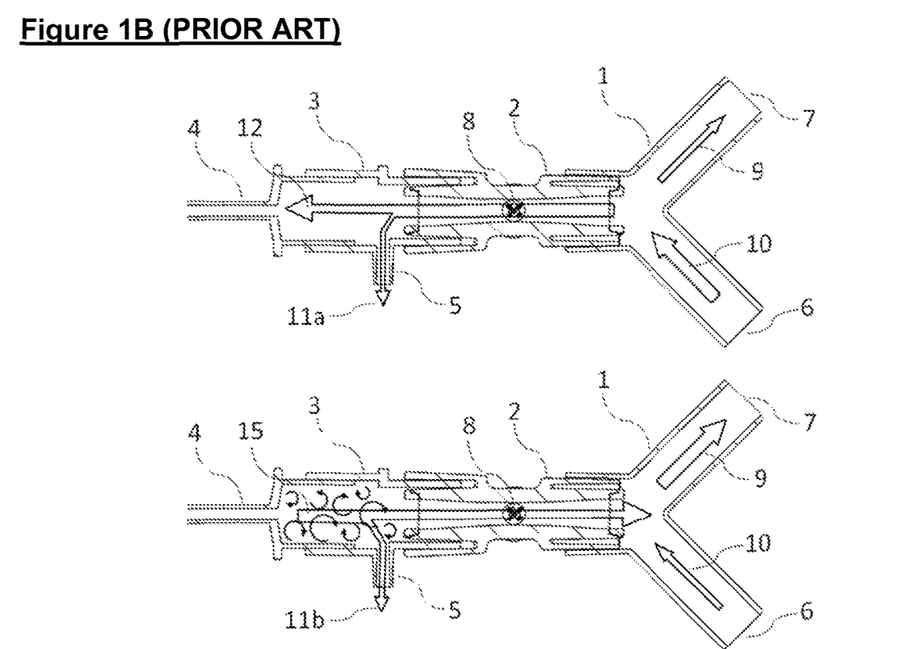
FIG. 1B shows two cross sections of the first prior art port configuration showing tidal gas flow in both directions.

FIGS. 1A and 1B illustrates the currently most commonly used combination system in the prior art, where a separate gas sampling adapter 3 with a gas sampling port 5 is inserted between the flow sensor 2 and the patient endotracheal tube 4. A patient circuit manifold 1 with an inlet port 6 and an outlet port 7 is connected to the input side of the flow sensor 2.

The series of connectors contribute to overall deadspace, which exceeds 2 ml. The multiplicity of sequentially arranged parts makes the total patient interface relatively long and heavy, which may also contribute to patient discomfort. The overlapping mating surfaces of the connectors introduces step contractions and expansions in the flow path, which gives rise to fluid mechanical inefficiencies and turbulence mixing. The multiplicity of adapter parts also increases the number of connector points, where interactions between manufacturing tolerances of injection moulded parts, from different producers, risk becoming a source of incompatibility and actual gas leaks. The first cross-sectional view in FIG. 1B shows how a sampling gas portion 11a is diverted from the inhaled gas flow 12. The sampling gas portion 11a was measured by the flow transducer 8, but does not form part of the actual inhaled tidal volume.

FIG. 1B also shows in the second cross section how a sampling gas portion 11b is also diverted from the exhaled gas flow 15 before the flow transducer 8 and it exits with the exhaled flow 9 through the outlet port 7 of the patient circuit manifold. The sampling gas 11b originates from the exhaled tidal volume, but is not measured by the flow transducer 8. This configuration results in a tidal volume measurement error. Also, the discrepancy between inhaled and exhaled tidal volume manifests as a rogue leak measurement. The expansion and deadspace within the gas sampling adapter 3 causes mixing in the exhaled gas flow 15, which affects accuracy in the gas concentration measurement.

Figure 1C:
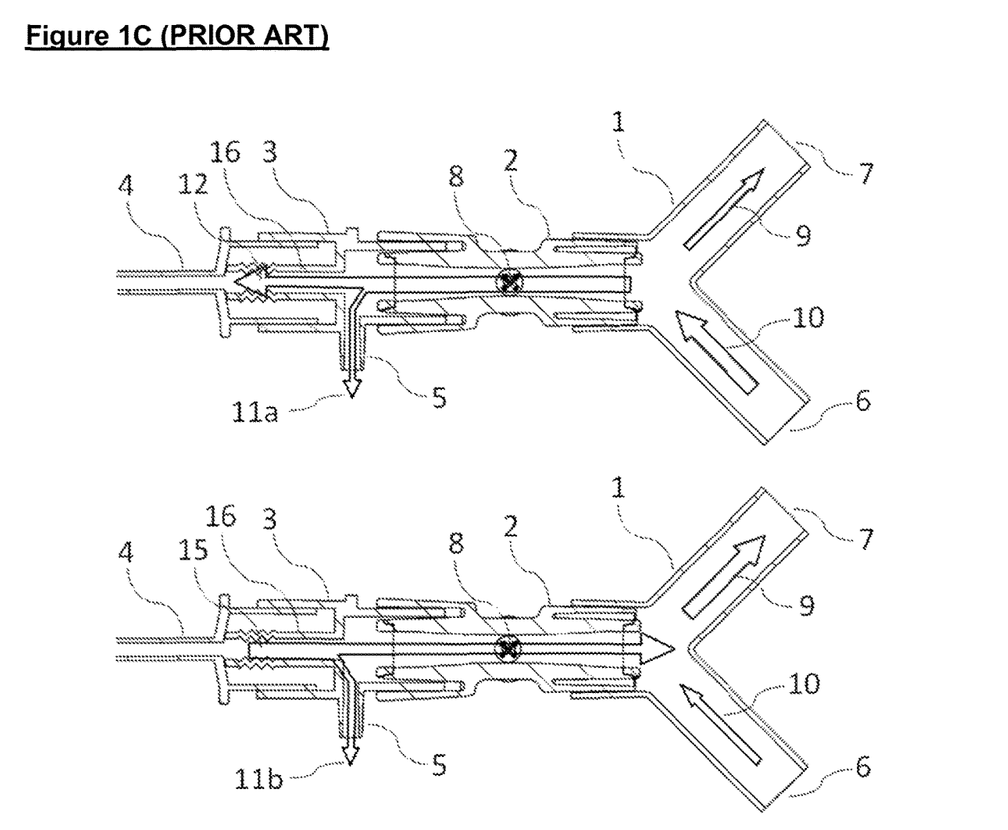
FIG. 1C show two cross sections of a second prior art port configuration similar to the first showing tidal gas flow in both directions.

The cross-sectional view in FIG. 1C shows a second example prior art solution that is similar but aims to reduce the deadspace with an axially compressible tube member 16 inserted into the gas sampling adapter 3, which can improve the gas concentration measurement aspect.

Figure 2A:
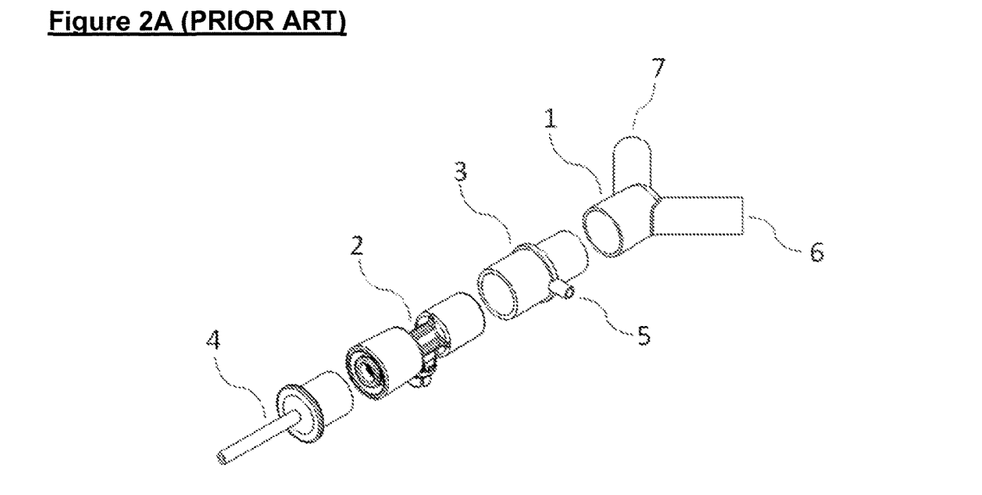
FIG. 2A shows an exploded perspective view of a third prior art port configuration.
Figure 2B:
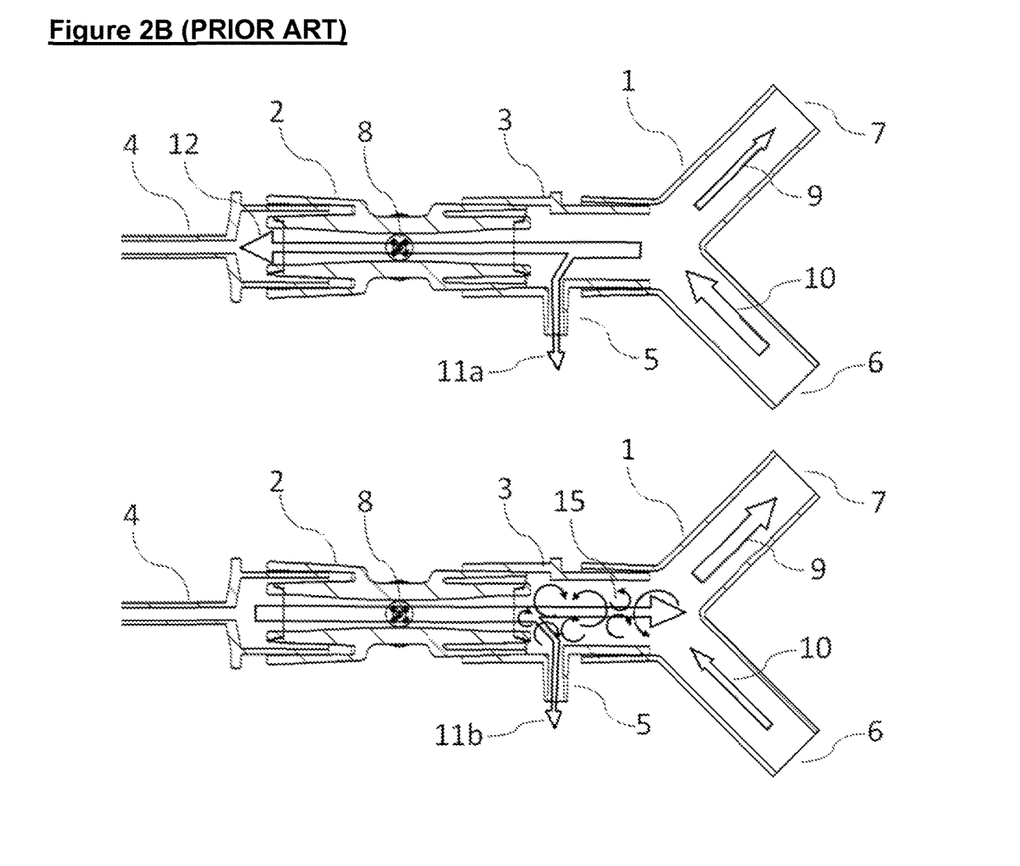
FIG. 2B shows two cross sections of the third prior art port configuration showing tidal gas flow in both directions.

FIG. 2A illustrates a third embodiment with the same parts as shown in FIG. 1A; but where the gas sampling adapter 3 is inserted between the flow sensor 2 and the patient circuit manifold 1. This configuration eliminates the tidal volume flow measurement error and the rogue leak measurement aspects. The cross-sectional views in FIG. 2B shows how the gas sampling port 5 is now situated in a space within which significant gas mixing occurs, due to the expansion in the exhaled gas flow 15 and the collision with the continuous fresh gas flow 10 from the patient circuit. This configuration causes a more severe deterioration in the concentration measurement aspect.

Figure 3A:
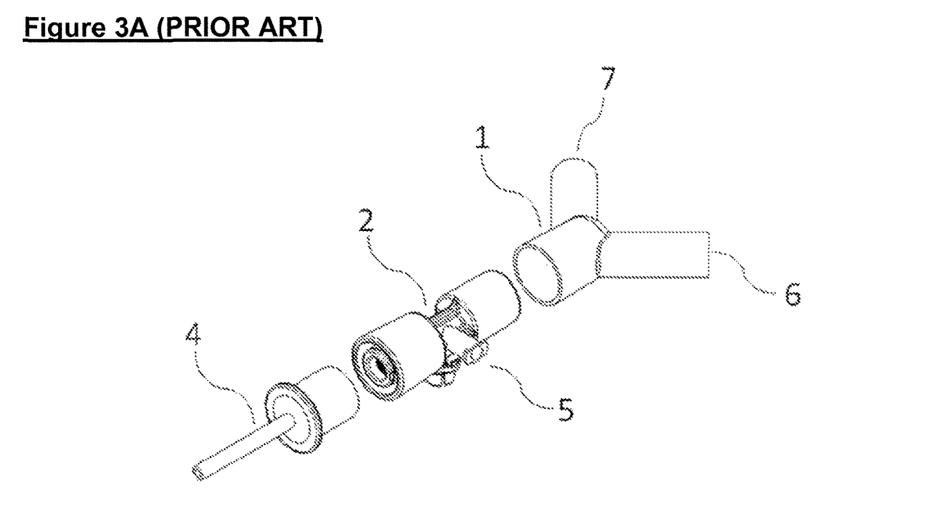
FIG. 3A shows an exploded perspective view of a fourth prior art port configuration.
Figure 3B:
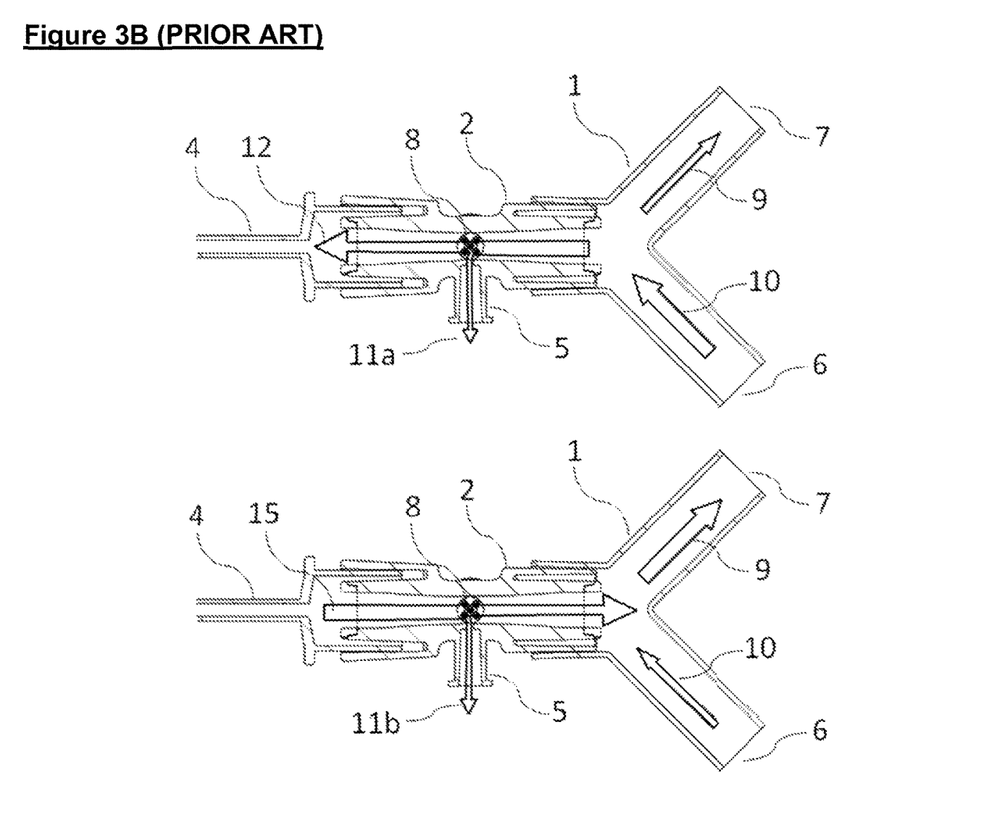
FIG. 3B shows two cross sections of the fourth prior art port configuration showing tidal gas flow in both directions.

FIG. 3A illustrates a fourth version of the prior art in which a flow sensor 2 integrating a gas sampling port 5, in an arrangement that is substantially equivalent to a prior art device marketed by Corscience GmbH & Co, Germany. The gas sampling port 5 is arranged centrally and symmetrically to the constant temperature anemometry wire elements of the flow transducer 8. A cross-sectional view in FIG. 3B shows how a sampling gas portion 11a, diverted from the inhaled gas flow 12, is partially measured by the flow transducer 8, but does not form part of the actual inhaled tidal volume. FIG. 3B also shows how a sampling gas portion 11b diverted from the exhaled gas flow 15 is partially measured by the flow transducer 8. Moreover, the gas sampling flow 11a and 11b is, typically, drawn by a reciprocal action vacuum pump, such as a piston or diaphragm type, which causes a pressure oscillation at the sampling port. At higher pumping rates, the pressure wave tends to cause an oscillating flow artefact across the flow transducer, which further influences the measurement accuracy. This arrangement can result in smaller errors, relative to the arrangement shown in FIG. 1b, but still causes an important tidal volume measurement error. Due to the fact that measurement errors in both inhaled and exhaled tidal volume in this arrangement are approximately the same, this arrangement eliminates the rogue leak measurement, but still suffers the problems mentioned above.

Figure 4:
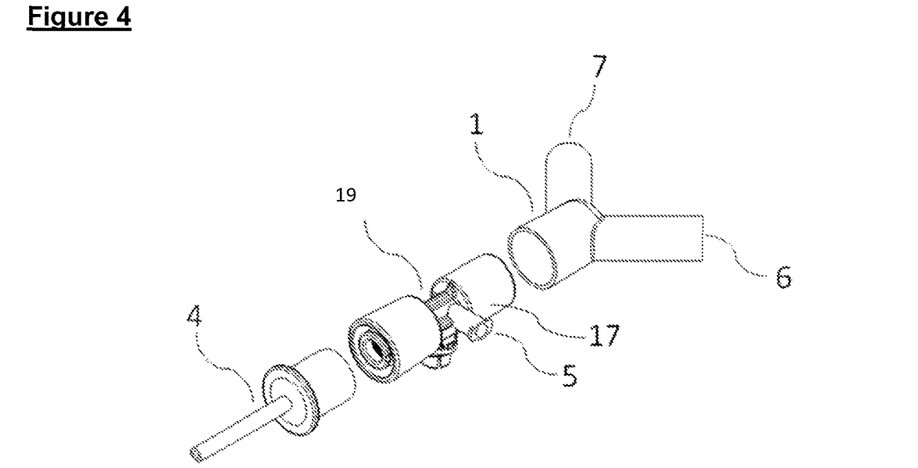
FIG. 4 shows an exploded perspective view of a first embodiment of gas flow sensor according to the present invention in a ventilator port configuration.

FIG. 4 shows an arrangement where a first embodiment of combined flow sensor 19 of the present invention is inserted between the patient endotracheal tube 4 and the patient circuit manifold 1. A gas sampling port 5 in the flow sensor 19 is arranged asymmetrically offset upstream from the flow transducer 8.

Figure 5:
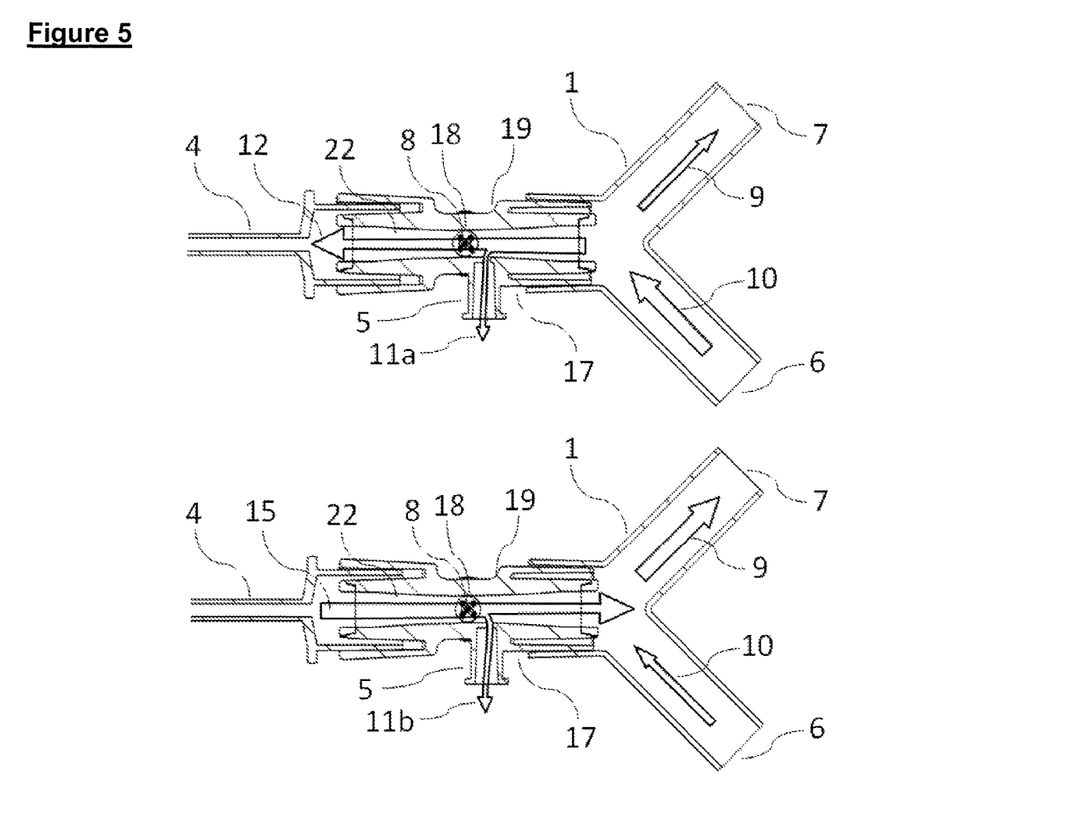
FIG. 5 shows two cross-sectional views of the assembled port configuration of FIG. 4 with the first embodiment of the present invention connected to associated patient interface components.

FIG. 5 is a cross-sectional view illustrating the present invention flow sensor 19 connected to the endotracheal tube 4 and patient circuit manifold 1. A sampling gas portion 11a is diverted from the inhaled gas flow 12 prior to reaching the flow transducer 8. FIG. 5 also shows how a sampling gas portion 11b is diverted from the exhaled gas flow 15 after flowing across the flow transducer 8. Subject to the important dimensions described under FIG. 6, this flow sensor 2 arrangement eliminates measurement errors in both inhaled and exhaled tidal volumes, and therefore does not produce any rogue leak measurement. The bi-directional flow transducer 8 part of the design is based on two constant temperature wires separated by an air resistance body, according to the principle described in U.S. Pat. No. 4,363,236. The transducer 8 has an electrical connection plug 18 in the outside of the flow sensor 19 so that it may be connected to equipment for analysis. The nature and configuration of that plug will of course depend on the item to which it is to be connected.

In a typical practical application the sampling gas 11a or 11b flow rate is between 50 ml/min and 150 ml/min. Testing of the configuration in FIG. 5 has confirmed the flow transducer 8 maintains acceptable performance with gas sampling flow rates up to 500 ml/min. Beyond this point, both the volume measurement error and rogue leak measures may become unacceptable.

The flow sensor 19 defines a flow path 22 therethrough. At the open ends of which are low resistance stainless steel meshes 13 and 14. These meshes helps reduce mixing between adjacent gas volumes, by breaking down larger turbulence eddies into smaller ones, to more closely approximate a laminar flow. The meshes have a secondary purpose in protecting the fragile flow transducer 8 wires from damage by foreign objects—for example, during cleaning. The remaining parts of the sensor may comprise plastic such as polycarbonate or polysulfone.

Figure 6:
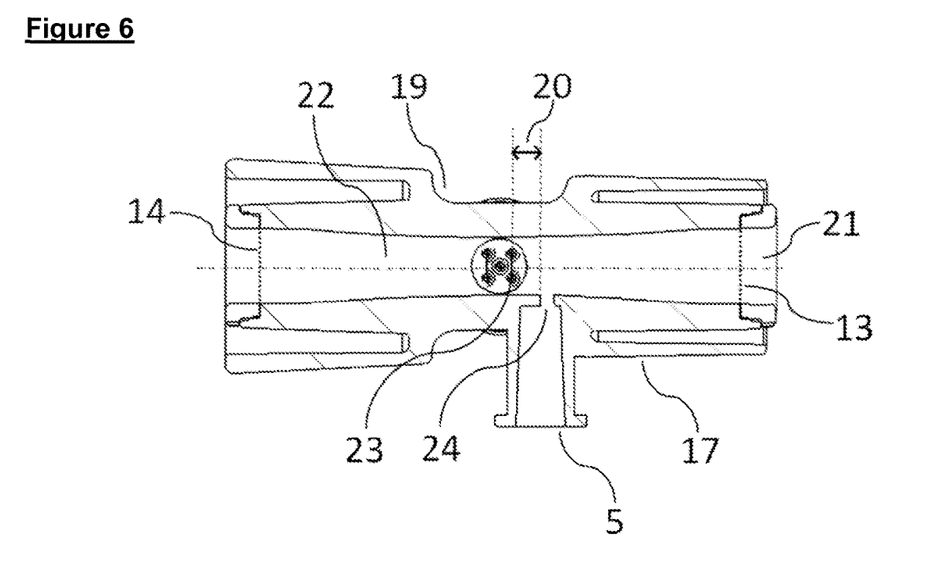
FIG. 6 shows a cross-sectional view of the first embodiment of gas flow sensor of the present invention.

FIG. 6 shows a cross-section of the present invention flow sensor 19 along its length. In this embodiment the tubular flow path 22 is 44 mm long with an average diameter of 5.5 mm, which equates to a deadspace of 1.05 ml. When discounting the space saving in overlapping connectors, the net additional deadspace attributable to the flow sensor 19 is 0.8 ml. Flow resistance through the flow sensor 19 is 0.12 mbar/l/min at a 10 l/min flow rate. The tidal gas flow is never perfectly free from turbulence and the gas sampling pump can also create a flow noise artefact. An aim of the present invention is to prevent gas that has passed over the flow transducer 8 and contributed to an inhaled tidal volume measurement, from subsequently be drawn into the gas sampling port 5. The separation distance 20 between the nearest flow transducer wire 23 and the leading circumferential edge of the hole 24 breaking through the flow sensor wall to the sampling port 5, in the axial direction towards the upstream opening 21, has an important effect on the flow transducer 8 performance. It has been found that a separation distance (labelled 20 in FIG. 6) of substantially 3 mm fully eliminates any adverse measurement effect over the therapeutic tidal flow ranges and for gas sample flow rates up to 150 ml/min, and assures acceptable performance, with only a tolerable minor error, up to gas sample flow rate up to 500 ml/min. Further increasing the separation distance 20 will require the flow sensor 2 be increased in length, to prevent the sampling port 5 encroaching on the mandatory 16 mm long connector mating surface 17. Increasing the separation distance 20 up to 10 mm would increase the net deadspace by 0.2 ml to the maximum tolerable 1 ml.

The gas sampling port 5 has a Luer lock fitting, but may be changed for any alternative connector standard. The hole 24 linking the internal gas flow path 22 to the gas sampling port 5 is 1.5 mm in diameter and is offset within the female mating part of the said port 5, to maximize the separation distance 20 for the given overall length of the flow sensor 19.

The invention claimed is:

1. A gas flow sensor for a ventilator, the gas flow sensor formed from a single component and comprising:
   a. a flow path extending between a first end that connects to a supply of gas and a second end that couples to a patient airway interface;
   b. a constant temperature anemometer sensor arranged within the flow path between those ends;
   c. a sampling port for coupling with a gas analyser device; and
   d. an orifice which is in fluid communication with the flow path and the sampling port so that in use gas can be drawn from the flow path for analysis, the gas being drawn through the orifice from the flow path at a position located between the anemometer sensor and the first end, wherein the distance between the orifice and the anemometer sensor is in the range of 3-10 mm.

2. A gas flow sensor as claimed in claim 1 wherein the flow path is defined by a substantially straight tubular passageway.

3. A gas flow sensor as claimed in claim 1 wherein the anemometer sensor comprises one or more wires arranged perpendicularly across, and substantially centrally within, the flow path.

4. A gas flow sensor as claimed in claim 3 wherein the anemometer sensor comprises two or more wires.

5. A gas flow sensor as claimed in claim 1 wherein at least one mesh is located across the flow path adjacent at least one of the first end and second end.

6. A gas flow sensor according to claim 1 wherein the gas is air or a mixture of air and at least one other gas or vaporized material.

7. A method of drawing sampling gas from the flow path of a ventilator including a constant temperature anemometer sensor arranged within that flow path, the anemometer sensor having wires, the method comprising:
   providing an orifice which is in fluid communication with the flow path on the upstream side of the anemometer sensor wires; and,
   drawing gas through the orifice from the flow path, the orifice provided at a distance of 3-10 mm from the sensor wires, and passing the drawn gas to a gas analyser device for analysis.

* * * * *